(12) United States Patent
Chu

(10) Patent No.: US 10,524,770 B2
(45) Date of Patent: Jan. 7, 2020

(54) MEDICAL DEVICE HANDLES AND RELATED METHODS

(71) Applicant: Boston Scientific Scimed, Inc., Maple Grove, MN (US)

(72) Inventor: Michael S.H. Chu, Brookline, MA (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 87 days.

(21) Appl. No.: 15/616,261

(22) Filed: Jun. 7, 2017

(65) Prior Publication Data

US 2017/0354404 A1    Dec. 14, 2017

Related U.S. Application Data

(60) Provisional application No. 62/347,697, filed on Jun. 9, 2016.

(51) Int. Cl.
*A61B 17/00* (2006.01)
*A61B 1/00* (2006.01)
*A61B 90/00* (2016.01)

(52) U.S. Cl.
CPC .... *A61B 17/00234* (2013.01); *A61B 1/00133* (2013.01); *A61B 2017/00296* (2013.01); *A61B 2017/00469* (2013.01); *A61B 2017/00477* (2013.01); *A61B 2017/00862* (2013.01); *A61B 2090/034* (2016.02)

(58) Field of Classification Search
None
See application file for complete search history.

(56) References Cited

U.S. PATENT DOCUMENTS

| 6,273,893 | B1  |   | 8/2001 | McAllen, III et al. |
| 6,540,722 | B1  |   | 4/2003 | Boyle et al. |
| 7,393,344 | B2  | * | 7/2008 | Mohammed ........ A61M 5/3232 604/195 |
| 8,992,470 | B2  |   | 3/2015 | Barenboym et al. |
| 2007/0135803 | A1 |  | 6/2007 | Belson |
| 2012/0078118 | A1 | * | 3/2012 | Jenkins .................. A61B 5/065 600/478 |

(Continued)

FOREIGN PATENT DOCUMENTS

EP    0607343 B1 * 3/2002    ........ A61M 39/0613

OTHER PUBLICATIONS

Robert W. Messler, "Joining of Materials and Structures: From Pragmatic Process to Enabling Technology", p. 98, Aug. 19, 2004, https://books.google.com/books?id=CRt97aa7cnMC&pg=PA97#v=onepage&q&f=false, viewed on Oct. 22, 2018.*

(Continued)

*Primary Examiner* — Christopher Koharski
*Assistant Examiner* — James Moss
(74) *Attorney, Agent, or Firm* — Bookoff McAndrews, PLLC

(57) ABSTRACT

A medical device may include a tool body and a handle. The handle may include a first body having a first coupling feature extending axially along the first body and a second body including a second coupling feature positioned within the first coupling feature. In a first orientation, the first body and second body may be rotatable and axially translatable relative to each other as a function of the first and second coupling features.

20 Claims, 5 Drawing Sheets

(56) References Cited

U.S. PATENT DOCUMENTS

2012/0259203 A1* 10/2012 Devereux ......... A61M 25/0631
600/414
2014/0257253 A1* 9/2014 Jemison ........... A61B 17/32056
606/1
2015/0164522 A1* 6/2015 Budiman ............. A61B 17/221
606/113

OTHER PUBLICATIONS

HeyCo Administrator, "The Advantages of Using A Rubber Grommet", Sep. 18, 2014, http://heyco.com/blog/advantages-using-rubber-grommet/, viewed on Oct. 23, 2018.*
International Search Report and Written Opinion for International Application No. PCT/US2017/036539, dated Sep. 8, 2017 (11 pages).

\* cited by examiner

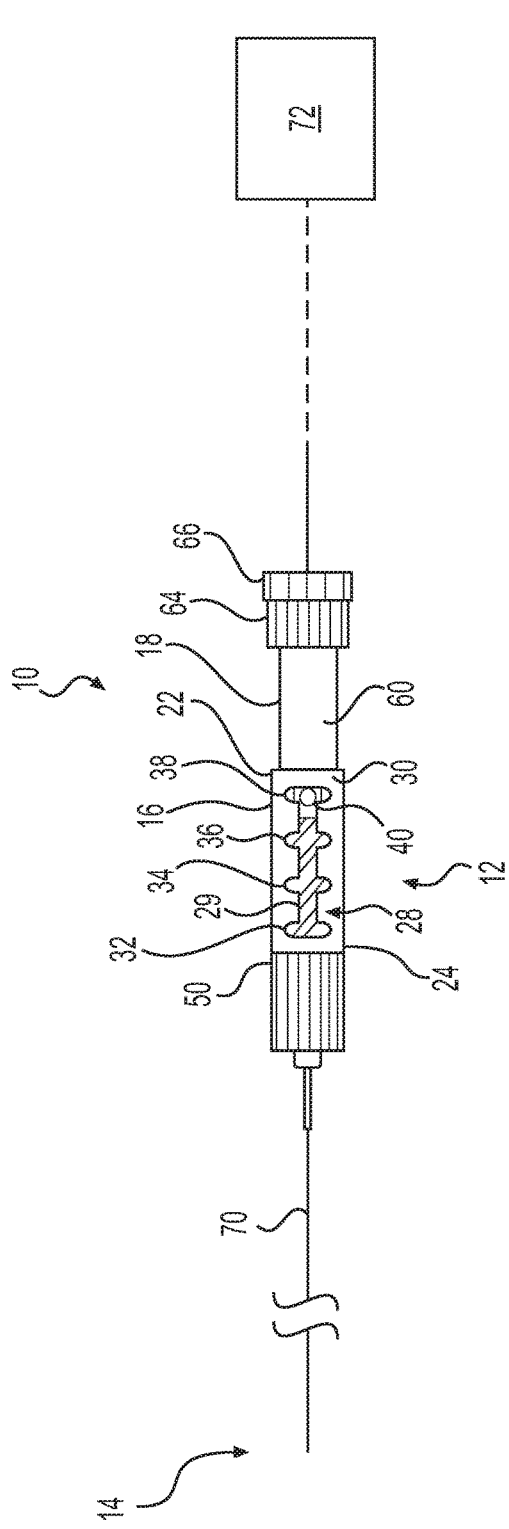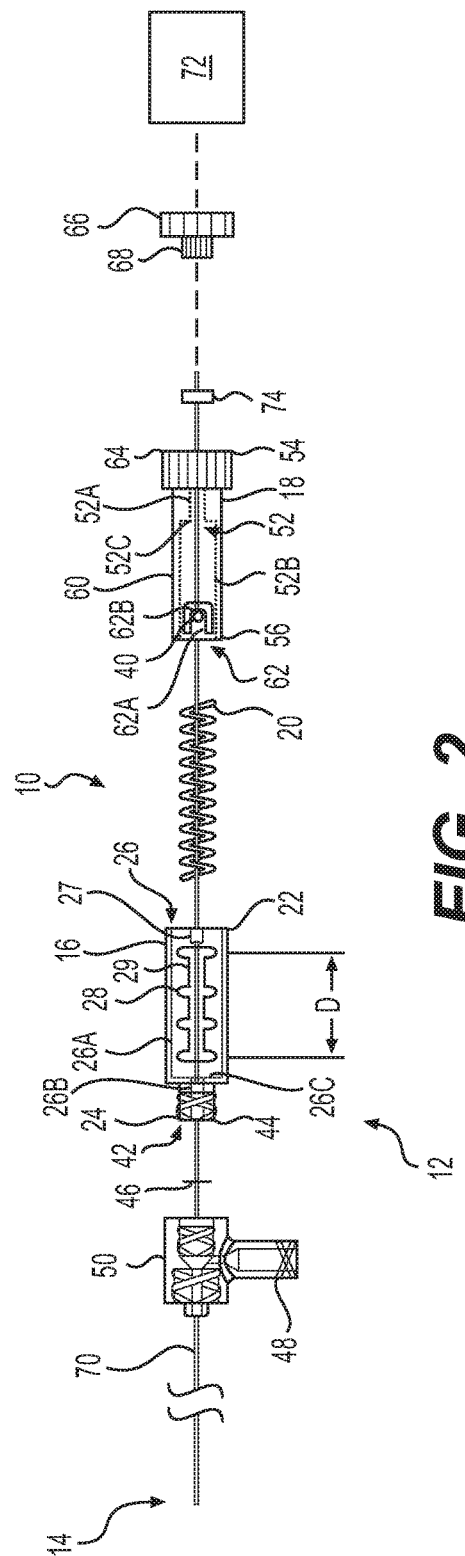

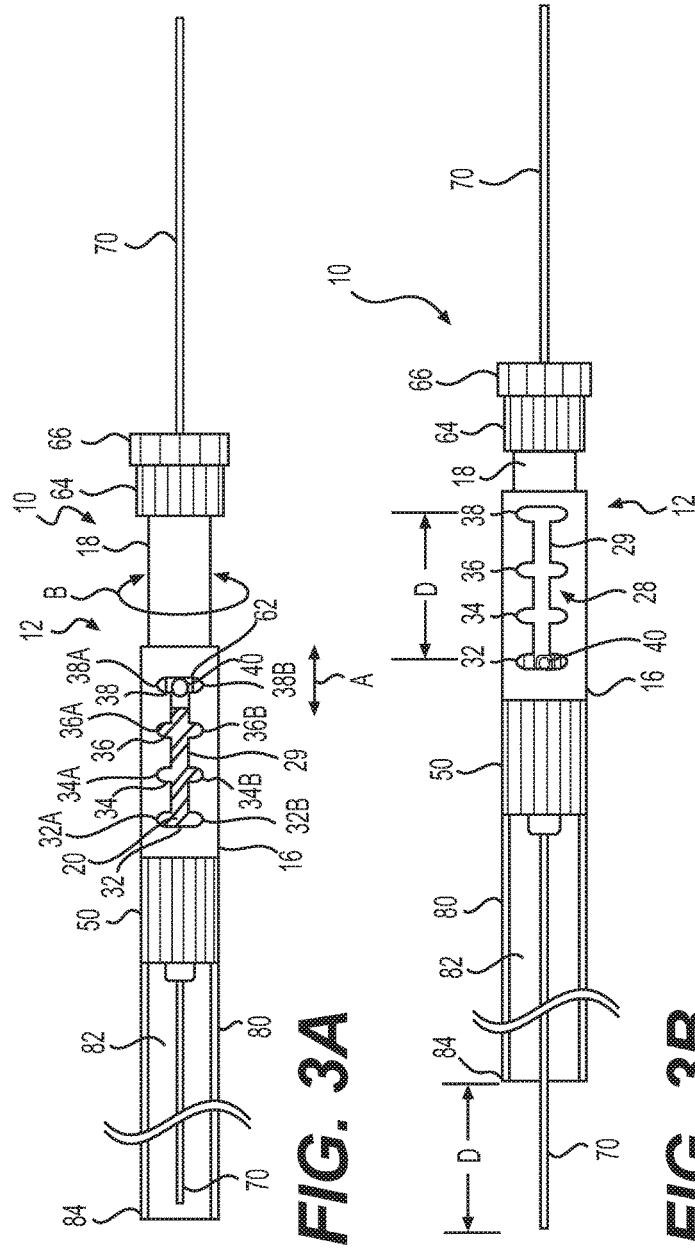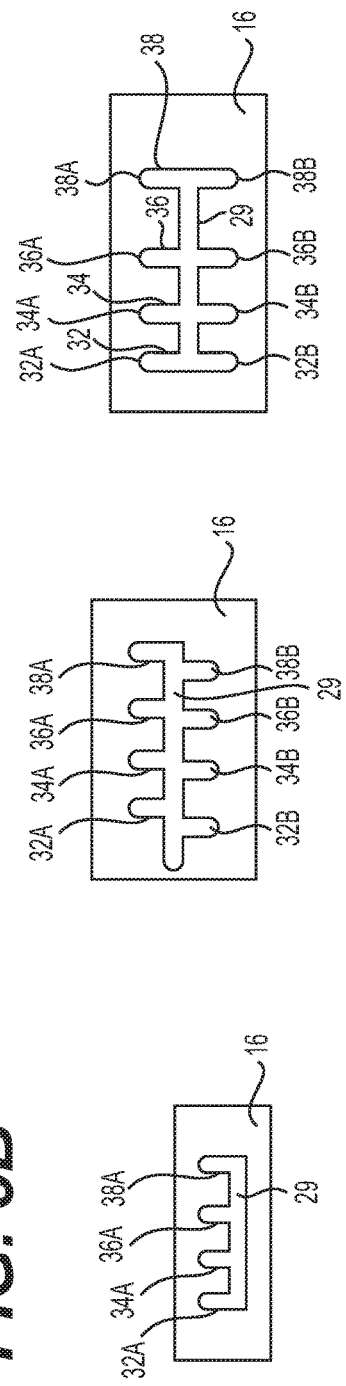

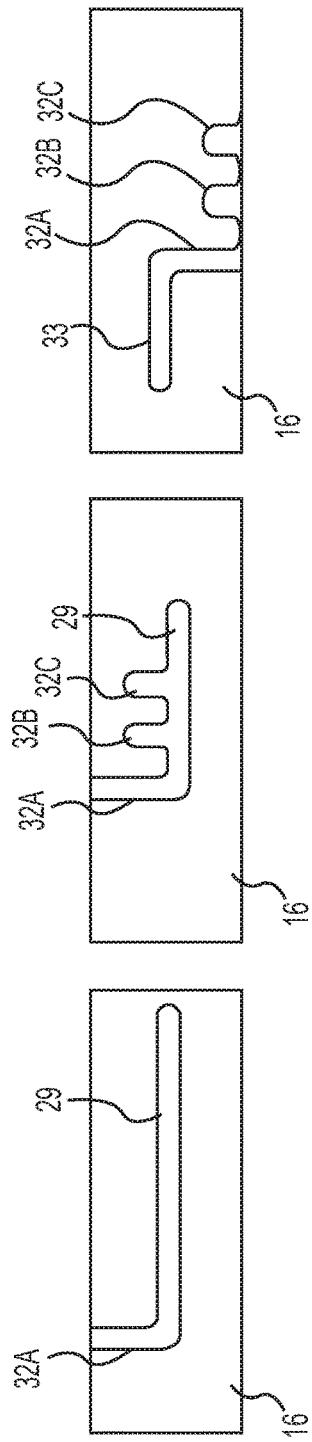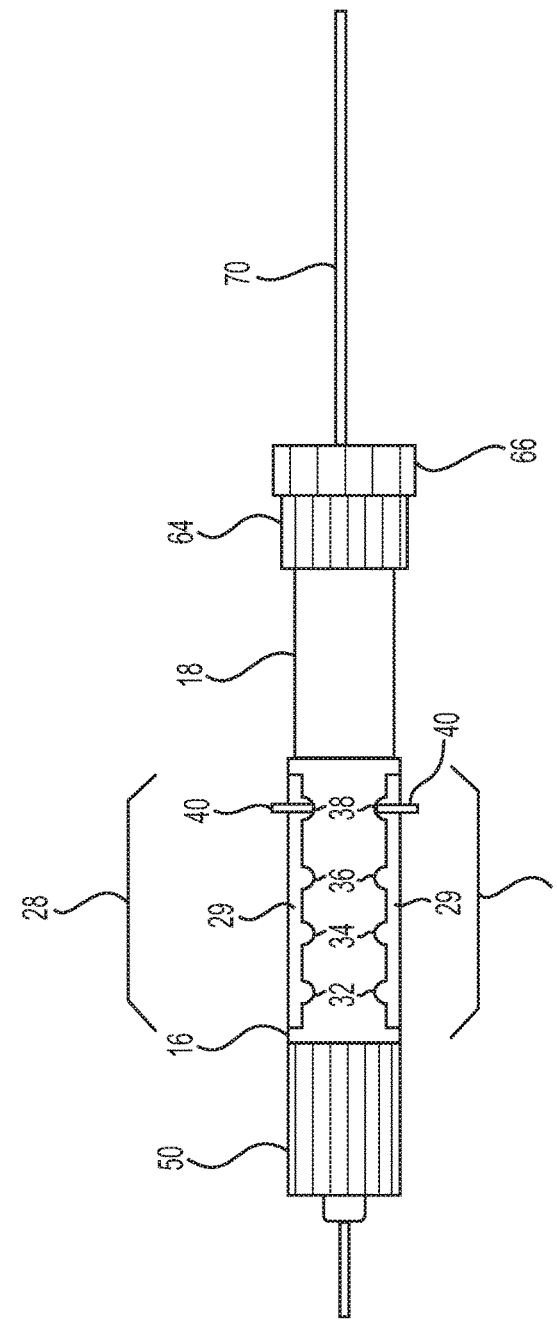

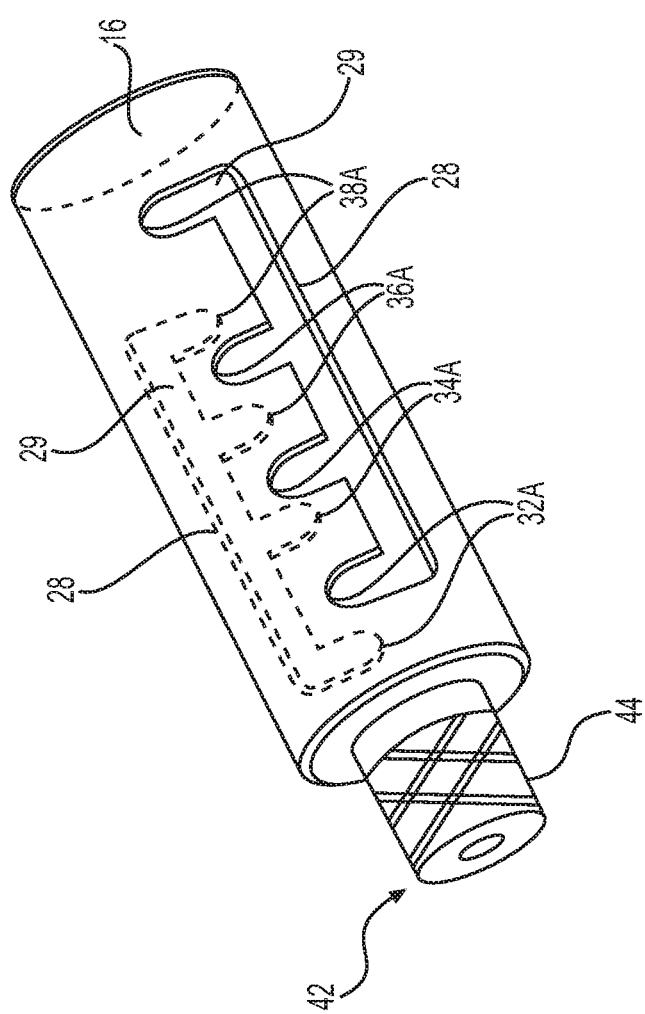

MEDICAL DEVICE HANDLES AND RELATED METHODS

CROSS-REFERENCE TO RELATED APPLICATIONS

This patent application claims the benefit of priority under 35 U.S.C. § 119 to U.S. Provisional Patent Application No. 62/347,697, filed Jun. 9, 2016, which is herein incorporated by reference in its entirety.

TECHNICAL FIELD

Various aspects of the present disclosure relate generally to medical device handles and related methods. More specifically, the present disclosure relates to medical device handles for delivering one or more tools.

BACKGROUND

Medical devices, such as lasers, needles, infusion tubes, sensors, and the like may include a tool (e.g., an elongate member, laser fiber, shaft, actuation line, luminal device, etc.), and may be arranged for delivery through a working channel of an insertion device (e.g., an endoscope such as, for example, a ureteroscope, a hysteroscope, a uteroscope, a bronchoscope, a cystoscope, and similar devices). The tool of such medical devices may be selectively extended and retracted relative to the working channel of the insertion device to deploy or retract the tool to perform one or more therapies, treatments, or diagnostic evaluations on a subject. For example, the medical device may include a laser having a laser body arranged for delivery through a working channel of a ureteroscope. However, if a working length of the laser body is too long relative to the length of the working channel of the ureteroscope, inadvertent tissue damage, improper alignment, and/or misfiring of the laser may occur. Further, if the working length of the laser body is too short relative to the length of the working channel of the ureteroscope, activation of the laser may burn or otherwise damage the ureteroscope, or fail to effectively treat the subject. As such, medical professionals must spend time tediously adjusting the working length of the laser body (or other such medical device) relative to the ureteroscope to ensure, upon deployment, the laser body extends the correct distance relative to the working channel of the ureteroscope. Such efforts may increase the length, cost, and/or complexity of the medical procedure.

The devices and methods of the current disclosure may rectify some of the deficiencies described above or address other aspects of the prior art.

SUMMARY

Examples of the present disclosure relate to, among other things, medical retrieval devices. Each of the examples disclosed herein may include one or more of the features described in connection with any of the other disclosed examples.

In one example, a medical device may include a tool body and a handle. The handle may include a first body having a first coupling feature extending axially along the first body and a second body including a second coupling feature positioned within the first coupling feature. In a first orientation, the first body and second body may be rotatable and axially translatable relative to each other as a function of the first and second coupling features.

Examples of the medical device may additionally include any one or more of the following features. The first coupling feature may include a track extending through a circumferential surface of the first body. The track may include a channel and a plurality of tabs extending from the channel. The plurality of tabs may extend radially outwardly from the channel. The plurality of tabs may be equispaced from one another. The plurality of tabs may include four tabs. The plurality of tabs may extend in a first direction and a second direction from the channel. The second coupling feature may include a pin. The pin may be positioned on a cantilevered support of the second body. The handle may further include a biasing member. The biasing member may be received within the first body and the second body. The second body may be positioned within the first body. The device may further include a cap coupled to a proximal end of the second body. The device may further include a grommet positioned about the tool body and arranged between the cap and the proximal end of the second body. In a second orientation, the first body and the second body may be rotatably and axially locked relative to each other.

In another example, a medical device may include an tool body terminating in an end effector and a handle The handle may include a first body having a track extending axially along the first body and a second body coupled to the first body and including a pin positioned within the track. In a first orientation, the first body and second body may be rotatable and axially translatable relative to each other. In a second orientation, the first body and second body may be rotatably and axially locked relative to each other.

Examples of the method may further include one or more of the following features. The track may extend through a circumferential surface of the first body and may include an channel and a plurality of tabs extending from the channel. The plurality of tabs may be equispaced from one another. Each of the plurality of tabs may extend in a first direction and a second direction from the channel. The method may further include a cap coupled to a proximal end of the second body, and a grommet positioned about the tool body and arranged between the cap and the proximal end of the second body, in a first configuration, the tool body may be moved axially relative to the grommet, and in a second configuration, the tool body may be locked axially relative to the grommet. The pin may be positioned on a cantilevered support of the second body. The handle may further include a biasing member positioned within the first body and the second body.

In another example, a method may include delivering an tool body of a medical device through a working channel of an insertion device. The medical device may further include a first body and a second body. The method may further include moving a pin coupled to the second body axially along an channel of a track positioned on the first body and extending the tool body of the medical device distally of the working channel of the insertion device. Further, the method may include rotating the second body relative to the first body to position the pin within a tab of the track extending radially outwardly of the channel of the track.

Examples of the methods may further include one or more of the following features. The method may include rotating the second body relative to the first body to position the pin within the channel of the track, and axially retracting the pin along the channel of the track to retract the tool body relative to the working channel of the insertion device. The method may also include retracting the tool body relative to the working channel of the insertion device includes aligning a distal-most end of the tool body with a distal-most end of the working channel and further including axially securing the tool body relative to the second body via a grommet.

Both the foregoing general description and the following detailed description are exemplary and explanatory only and are not restrictive of the features, as claimed. As used herein, the terms "comprises," "comprising," or other variations thereof, are intended to cover a non-exclusive inclusion such that a process, method, article, or apparatus that comprises a list of elements does not include only those elements, but may include other elements not expressly listed or inherent to such a process, method, article, or apparatus. Additionally, the term "exemplary" is used herein in the sense of "example," rather than "ideal."

BRIEF DESCRIPTION OF THE DRAWINGS

The accompanying drawings, which are incorporated in and constitute a part of this specification, illustrate exemplary features of the present disclosure and together with the description, serve to explain the principles of the disclosure.

FIG. 1 illustrates an exemplary medical device having a handle and a tool body;

FIG. 2 illustrates an exploded view of the exemplary medical device of FIG. 1 including a connector having an additional branch;

FIGS. 3A and 3B illustrate the medical device of FIG. 1 in a retracted configuration and an extended configuration, respectively;

FIGS. 4A-4F illustrate additional exemplary slot bodies of the medical device of FIG. 1;

FIGS. 5A and 5B illustrate features of additional exemplary medical devices each having a handle and a tool body.

DETAILED DESCRIPTION

Figure 6:
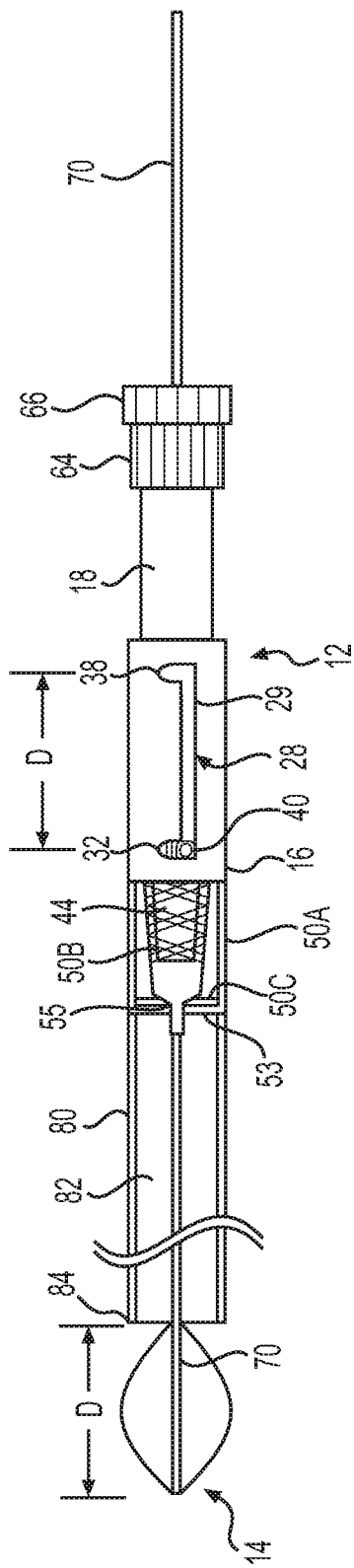
FIG. 6 illustrates a further exemplary medical device, according to aspects of this disclosure.

Examples of the present disclosure relate to medical device handles for deployment of a tool body of a medical device. The medical device may be delivered through any appropriate insertion device, and may include any one or more end effectors such as, e.g., a laser fiber, an irrigation and/or aspiration channel, or a needle, etc.

Reference will now be made in detail to examples of the present disclosure described above and illustrated in the accompanying drawings. Wherever possible, the same reference numbers will be used throughout the drawings to refer to the same or like parts.

The terms "proximal" and "distal" are used herein to refer to the relative positions of the components of an exemplary medical device or insertion device. When used herein, "proximal" refers to a position relatively closer to the exterior of the body or closer to an operator using the medical device or insertion device. In contrast, "distal" refers to a position relatively further away from the operator using the medical device or insertion device, or closer to the interior of the body.

FIG. 1 illustrates an exemplary medical device 10, including a handle 12 and a tool body terminating in an end effector 14. Handle 12 may include a slot body 16, a pin body 18, and a biasing member 20 (FIG. 2) positioned therebetween. Slot body 16 may include a proximal end 22 and a distal end 24 and may include a bore or lumen 26 (FIG. 2) therethrough. As shown in FIG. 2, for example, lumen 26 may have a varied dimension (e.g., diameter). For example, lumen 26 may have a first portion 26A adjacent proximal end 22 and a second portion 26B adjacent distal end 24. As shown, first portion 26A has a larger size, dimension, or diameter than second portion 26B. A protrusion, abutment wall, or surface 26C of slot body 16 may be positioned between first portion 26A and second portion 26B of lumen 26. Surface 26C may cooperate with biasing member 20, as will be described in further details below.

As shown in FIGS. 1 and 2, slot body 16 may include a slot track 28. Slot track 28 may extend through a side (e.g., circumferential) wall 30 of slot body 16. That is, slot track 28 may extend through the entire thickness of wall 30. Slot track 28 may include a channel 29 and a plurality of tabs 32, 34, 36, and 38. Tabs 32, 34, 36, and 38 may be spaced apart at increments denoting a degree of extension of a tool body 70 of medical device 10. For example, when pin 40 is positioned within tab 32, tool body 70 may be extended a maximum distance D (FIG. 3B) relative to an insertion device 80. Additionally, when pin 40 is positioned within tab 38, tool body 70 may be positioned within a working channel 82 of insertion device 80 (FIG. 3A), either slightly retracted, extended, or aligned with a distal-most end 84 of insertion device 80.

Channel 29 may axially extend along wall 30 from a location adjacent proximal end 22 towards a location adjacent distal end 24. Tabs 32, 34, 36, and 38 extend radially outwardly from channel 29. For example, each of tabs 32, 34, 36, and 38 may have a first portion 32A, 34A, 36A, and 38A, and a second portion 32B, 34B, 36B, and 38B (FIG. 3A). Each of tab portions 32A, 34A, 36A, 38A, 32B, 34B, 36B, and 38B may have a first end in communication with channel 29, a length extending circumferentially about at least a portion of slot body 16, and a second end spaced from channel 29. Each of tab portions 32A, 34A, 36A, 38A, 32B, 34B, 36B, and 38B may cooperate with a protrusion, rod, or pin 40, as will be described in more detail below. Distal end 24 of slot body 16 may include a luer 42 (FIG. 2). Luer 42 may be a male medical (e.g., threaded) or slip luer and may include a male cooperative member 44. Additionally, luer 42 may cooperate with a connector 50, as will be described in further detail below.

Pin body 18 may be slidably and rotatably disposed within first portion 26A of lumen 26. As such, pin body 18 main have a main body 60 having a dimension, size, or diameter sized to be received within first portion 26A. Accordingly, main body 60 may have a dimension, size, or diameter smaller than a dimension, size, or diameter of first portion 26A. Pin body 18 may have a proximal end 54, a distal end 56 and a lumen 52 extending therebetween (FIG. 2). As shown in FIG. 2, for example, lumen 52 may have a varied dimension (e.g., diameter). For example, lumen 52 may have a first portion 52A adjacent proximal end 54 and a second portion 52B adjacent distal end 56. As shown, second portion 52B has a larger size, dimension, or diameter than first portion 52A. A protrusion, abutment wall, or surface 52C of slot body 16 may be positioned between first portion 52A and second portion 52B of lumen 52. Surface 52C may cooperate with biasing member 20, as will be described in further details below. Alternatively, a distal-most end of pin body 18 may cooperate with biasing member 20.

Pin body 18 may include a cantilevered support 62, as shown in FIG. 2. For example, support 62 may include a tab or projection moveable relative to main body 60. That is, support 62 may include a first portion 62a coupled to or monolithically formed with main body 60 while a second portion 62B is free or uncoupled from main body 60. In some arrangements, support 62 may be formed as a onepiece construction with main body 60, and then cut (e.g., via a laser or knife) along second portion 62b such that support 62 may bend or flex along first portion 62A. For example, second portion 62Bb can move relative to main body 60 by bending or flexing radially towards or away from a central longitudinal axis of main body 60. In addition, support 62 may support pin 40 thereon. For example, pin 40 may extend through support 62 and radially outward, away from the central longitudinal axis of main body 60. While not shown, pin 40 may include a hook or L-shape so as to facilitate maintaining pin 40 within slot track 28.

Additionally, pin body 18 may include a coupling member 64. Coupling member 64 may include an inner lumen (not shown) configured to receive a threaded or ribbed stem 68 of a cap 66. The inner lumen of coupling member 64 may be threaded or ribbed so as to cooperate with threaded or ribbed stem 68. While stem 68 and the inner lumen of coupling member 64 are described as threaded or ribbed, the disclosure is not so limited. Rather, stem 68 may be retained (e.g., either temporarily or permanently) within the lumen of coupling member 64 in any appropriate manner such as, for example, a pressure fit connection, an interference fit connection, adhesives, mechanical fasters (e.g., screws, pins, latch, etc.) or the like without departing from the scope of the disclosure.

As shown in FIG. 1, pin body 18 may be movably coupled to slot body 16. As such, main body 60 and support 62 may be inserted into first portion 26A of lumen 26 of slot body 16. For instance, in some arrangements, first portion 26A of lumen 26 may include an angled surface, taper, or ramp 27 (FIG. 2) which may facilitate guiding pin 40 towards and into channel 29. When main body 60 is inserted within lumen 26, pin 40 may contact or press against ramp 27 and/or an inner surface or wall of lumen 26. Upon such contact, support 62 may be caused to bend or flex radially inwardly toward the central longitudinal axis of main body 60. Continued advancement of pin body 18 into lumen 26 of slot body 16 will align pin 40 with slot track 28. Once pin 40 is positioned within slot track 28, support 62 may bend or flex radially outwardly away from the central longitudinal axis of main body 60 to maintain pin 40 within slot track 28. In other words, pin body 18 may be coupled to slot body 16 via a snap-fit arrangement.

Once pin 40 is received within slot track 28, pin 40 may be moved relative to slot track 28. For example, when pin 40 is located within channel 29, pin 40, and therefore pin body 18, may be advanced and retracted axially in the direction of arrow A (FIG. 3A) relative to slot body 16. Upon axial advancement or retraction of pin 40 relative to channel 29, pin 40 may be aligned with one or more of tabs 32, 34, 36, and 38. Once aligned, pin body 18 may rotated relative to the longitudinal axis of slot body 16, for example, in the direction of arrow B (FIG. 3A), so as to move pin 40 into one of tabs 32, 34, 36, and 38. For example, upon alignment of pin 40 with tab 32, pin body 18 may be rotated in a first direction (e.g., clock-wise) to locate pin 40 within first portion 32A of tab 32. Alternatively, pin body 18 may be rotated in a second direction (e.g., counter clock-wise) to locate pin 40 within a second portion 32B of tab 32. In either manner, pin 40 may be retained within tab 32.

In such a manner, slot body 16 and pin body 18 may be coupled together. Biasing member 20 may be positioned within first portion 26A of lumen 26 and second portion 52B of lumen 52 so as to bias or oppose slot body 16 and pin body 18. For instance, a distal end of biasing member 20 may abut or contact surface 26C while a proximal end of biasing member 20 may abut or contact surface 52C. Alternatively, a distal-most end of pin body 18 may abut or contact a proximal end of biasing member 20. As such, biasing member 20 may urge or push slot body 16 away from pin body 18. Accordingly, when pin body 18 is rotated so as to position pin 40 within channel 29, biasing member 20 may oppose surfaces 26C and 52C to urge pin 40 toward a proximal end of channel 29 adjacent tab 38. In other words, biasing member 20 may enable automatic retraction of pin 40 relative to channel 29 when pin 40 is not positioned, housed, or otherwise received within one of tabs 32, 34, 36, and 38. Alternatively, in some arrangements biasing member 20 may be omitted. As such, retraction of pin body 18 may be achieved manually. For example, a medical professional may manually pull pin body 18 and/or push slot body 16 relative to one another to move pin 40 proximally along channel 29. Biasing member 20 may be, for example, a helical spring (e.g., a compression spring), as shown in FIG. 2.

As noted above, medical device 10 may include any one or more end effectors 14 such as, e.g., a laser fiber, an irrigation and/or aspiration channel, a basket, a snare, a forceps, an angled member, or a needle, etc. For example, as shown in FIGS. 1 and 2, end effector 14 may include a laser having a tool body 70. Tool body 70 may be operably coupled to a source of laser energy 72. In another arrangement, however, end effector may be an irrigation and/or aspiration channel, a sensor, and/or a needle. In such arrangements, tool body 70 may be coupled to a source of fluid or vacuum, as appropriate. Tool body 70 may be coupled to handle 12 in any appropriate manner. For example, a grommet 74 (FIG. 2) may be positioned about tool body 70. Grommet 74 may be comprised of a compressible material such as, e.g., rubber. Upon threading or otherwise coupling stem 68 of cap 66 in the inner lumen (not shown) of coupling member 64, grommet 74 may compress, pinch, or otherwise grip tool body 70. In such a manner, tool body 70 may be fixedly coupled to pin body 18 of handle 12. Accordingly, axial or rotational movement of pin body 18 results in likewise movement of tool body 70, and consequently, end effector 14. Additionally, unscrewing or otherwise uncoupling cap 66 from coupling member 64 may enable grommet 74 to release tool body 70. As such, a position of tool body 70 relative to handle 12 may be adjusted, as needed. This may allow a user to adjust a working length of tool body 70 to a desired value.

As shown in FIG. 2, handle 12 of medical device 10 may be coupled to a connector 50. Connector 50 may be a port coupling of any appropriate insertion device (not shown) such as, for example, an endoscope (e.g., a ureteroscope, a hysteroscope, a ureteroscope, a bronchoscope, a cystoscope, and similar devices). Connector 50 may include two branches, as shown in FIG. 1. Optionally, however, connector 50 may include an additional branch 48 as shown in FIG. 2. Branch 48 may be coupled or uncoupled to one or more additional medical devices and/or one or more sources of aspiration/irrigation fluid. As shown, male cooperative member 44 of luer 42 may be threaded so as to cooperate with any appropriate threaded port of connector 50, as is known. Optionally, luer 42 may be a female luer (not shown) cooperatively arranged to receive a male luer port of connector 50, without departing from the scope of this disclosure. In either manner, handle 12 may be directly coupled to the connector 50 of any appropriate insertion device. In the arrangement described herein, a seal 46 may be positioned about tool body 70 axially between male cooperative member 44 and connector 50. That is, seal 46 may be disposed within connector 50 and proximal of a distal-facing surface of male cooperative member 44 to prevent proximal leakage of fluid along tool body 70. Seal 46 may be a wiper seal, a diaphragm, or like, and may be comprised of one or more of a silicone, a low durometer rubber, or like material. Seal 46 may seal without requiring additional accessories such as, e.g., an introducer and an additional seal coupling. Further, in some arrangements, connector 50 may be a rotating male luer, as will be described in further detail below.

As noted above, connector 50 may be a port coupling of any appropriate insertion device and as such, may be in communication with a working channel of the insertion device. For example, as schematically illustrated in FIGS. 3A and 3B, connector 50 may be a port coupling of an insertion device 80 having a working channel 82 and a distal-most end 84. Accordingly, coupling of connector 50 to handle 12 of medical device 10 may enable tool body 70 of medical device 10 to be delivered through working channel 82 of insertion device 80.

In use, grommet 74 may be positioned about tool body 70. Stem 68 of cap 66 may be introduced into the inner lumen of coupling member 64, thereby compressing grommet 74 to pinch, clasp, or grip tool body 70. As such, tool body 70 may be locked or held in position relative to handle 12 due to the compression of grommet 74 about tool body 70. Pin body 18 may be inserted within first portion 26A of lumen 26 of slot body 16. Initially, upon coupling pin body 18 and slot body 16 to one another, pin 40 may be received within tab 38, or within channel 29 adjacent tab 38 as shown in FIG. 3A. In such an arrangement, a distal-most end of tool body 70 may be positioned adjacent distal-most end 84 of working channel 82 of insertion device 80. Upon determining a need or desire to extend tool body 70 of medical device 10 distally of distal-most end 84 (e.g., to perform one or more therapies, treatments, or diagnostic evaluations on a subject), pin body 18 may be rotated so as to move pin 40 from within tab 38 towards channel 29. Alternatively, pin 40 may already be located within channel 29 adjacent tab 38, as shown in FIG. 3A. In either case, upon locating pin 40 within channel 29, pin body 18 may be advanced distally relative to slot body 16 in the direction A. In so doing, the distal-most end of tool body 70 may extend distally beyond distal-most end 84 of working channel 82. Upon advancing pin 40 along channel 29 a desired distance, pin body 18 may be rotated relative to slot body 16 so as to position pin 40 within one of tabs 32, 34, and 36, and retained therein. Upon determining a need or desire to retract tool body 70 of medical device 10, pin body 18 may be rotated relative to slot body 16 to return pin 40 to a location within channel 29, and retracted axially along channel 29 towards tab 38.

Tabs 32, 34, 36, and 38 may be spaced apart at increments denoting a degree of extension of tool body 70 of medical device 10. For example, positioning of pin 40 adjacent or within tab 38 may denote a configuration in which distal-most end of tool body 70 is positioned adjacent the distal-most end 84 of working channel 82. Tabs 34, 36, and 38 may denote a configuration in which the distal-most end of tool body 70 is positioned at increasingly distal locations distal of distal-most end 84 of working channel 82. For instance, positioning of pin 40 within or adjacent tab 32 may cause tool body 70 to extend a maximum distance D distal of distal-most end 84 of working channel 82. That is, as shown in FIG. 3B, the spacing between tab 32 and tab 38 may define a maximum distance D of extension of tool body 70 relative to distal-most end 84 of working channel.

While four tabs 32, 34, 36, and 38 are illustrated, the disclosure is not limited. Rather, more or less tabs may be positioned along slot body 16. For example, between about two and about ten tabs may be positioned along slot body without departing from the scope of this disclosure. As used herein, the terms "about," "substantially," and "approximately," indicate a range of values within +/−5% of a stated value. Additionally, while tabs 32, 34, 36, and 38 are illustrated as equispaced and having first and second portions aligned with one another, other arrangements of tabs are envisioned. For instance, as shown in FIG. 4A, each tab 32, 34, 36, and 38 may have only a single portion 32A, 34A, 36A, and 38A. That is, as opposed to the arrangements shown in FIGS. 1-3B in which each tab has a first portion (32A, 34A, 36A, and 38A) and a second portion (32B, 34B, 36B, and 38B), the arrangement of FIG. 4A includes only first portions 32A, 34A, 36A, and 38A and omits second portions 32B, 34B, 36B, and 38B. In another arrangement, as shown in FIG. 4B, first portions 32B, 34A, 36A, and 38A are axially offset from second portions 32B, 34B, 36B, and 38B. Additionally, as shown in FIG. 4C, tabs 32, 34, 36, and 38 are axially non-equispaced. That is, a spacing between adjacent tabs 32, 34, 36, and 38, may be non-uniform. In some arrangements, as shown in FIG. 4D, only one tab (e.g., tab 32A) may extend from channel 29. In such an arrangement, tab 32B may extend about 90° around the circumference of slot body 16. Further, as shown in FIGS. 4E and 4F (the view illustrated in FIG. 4F being rotated 90° about the longitudinal axis of slot body 16 relative to the view illustrated in FIG. 4E), one or more tabs (e.g., tabs 32A, 32B, and 32C) may extend from channel 29 in a direction perpendicular to a longitudinal axis of slot body 16. In addition, a release slot 33 may extend parallel with a longitudinal axis of slot body 16 from an end of tab 32A opposite that of channel 29. That is, when pin 40 (FIGS. 1, 2, 3A, and 3B) is advanced along channel 29 so as to align with tab 32A, pin 40 may be rotated relative to slot body 16 so as to enter tab 32A in a direction perpendicular to the longitudinal axis of slot body 16. If it is determined that an over extension/expansion of end effector 14 (e.g., a basket) is required or deemed desirable (e.g., to expand end effector 14 to a sufficiently large state so as to enable release of an oversized stone or other such material), pin 40 may be advanced distally along release slot 33, thereby enabling an over extension/expansion of end effector 14. Further, in some arrangements, one or more of tabs 32-38 may extend circumferentially about slot body 16 to a greater extent than at least one other of tabs 32-38. In such a manner, increased rotation of tool body 70 may be achieved.

In another arrangement, as shown in FIG. 5A, slot body 16 may include two slot tracks 28. Each slot track 28 may include a plurality of tabs 32, 34, 36, and 38 and an channel 29 (not shown in FIG. 5A, see FIGS. 1-4). In such an arrangement, pin body 18 may include two supports 62 (not shown in FIG. 5A) each including a pin 40. Extension and retraction of tool body 70 of FIG. 5A may be done in a manner similar to that as described above in connection with FIGS. 3A and 3B. As such, rotation of pin body 18 relative to slot body 16 may align pins 40 within channels 29 (see, for example, FIG. 2), and therefore, enable extension of tool body 70 relative to distal most end 84 of working channel 82 (see, for example, FIGS. 3A and 3B). In another arrangement, slot tracks 28 may omit channels 29. As such, each track may only include tabs 32, 34, 36, and 38 and advancement between tabs 32, 34, 36, and 38 may be accomplished by pushing pins 40 radially inwardly toward the central longitudinal axis of pin body 18, pushing pin body 18 distally relative to slot body 16, and enabling pins 40 to emerge through a tab 34, 36, or 38 distal to the tab 32, 34, or 36 from which pins 40 originated. Optionally, as shown in FIG. 5B, each of the plurality of tabs 32, 34, 36, and 38, of each slot track 28, may have only a single portion 32A, 34A, 36A, and 38A extending from a respective channel 29 radially around slot body 16 similar to the arrangement shown in FIG. 4A. When viewed from one of the ends of slot body 16, portions 32A, 34A, 36A, and 38A of each channel 29 extend from their respective channel in the same direction (clockwise or counterclockwise, depending on the end from which slot body 16 is viewed). As such, rotating pin body 18 in a first direction may cause pins 40 to engage tabs 32, 34, 36, and 38 of each slot track 28, and rotating pin body 18 in a second direction (opposite the first direction) may free pins 40 from tabs 32, 34, 36, and 38 of each slot track 28.

In another arrangement, as shown in FIG. 6, tool body 70 may be coupled to an expandable end effector 14. End effector 14 may include an expandable basket, forceps, and/or snare device. The tool body 70 and expandable end effector 14 may be "sheathless." That is, expandable end effector 14 may be self-expandable upon the removal of a constraining force. For instance, when positioned within working channel 82 of insertion device 80, end effector 14 may assume an at least partially collapsed state, and when positioned distally of working channel 82, end effector 14 may assume a radially expanded state. In other words, interaction between the end effector 14 and working channel 82 (or lack thereof) may cause end effector 14 to move between the collapsed and expanded states and no sheath or additional structure is required to limit expansion of end effector 14.

As shown in FIG. 6, slot track 28 includes only two tabs, e.g., tab 32 and tab 38, spaced a distance D apart. Optionally, tab 38 may be omitted, thus resulting in a single tab 32 along slot track 28 (e.g., FIG. 4D). Further, connector 50 may be a rotating male luer as schematically illustrated in FIG. 6. That is, connector 50 may include a first portion 50A and a second portion 50B. Second portion 50B may be coupled to slot body 16 via male cooperative member 44 of luer 42, as discussed above. Additionally, first portion 50A may be coupled to insertion device 80. First portion 50A and second portion 50B may be rotatable relative to one another. For instance, first portion 50A may rotatably receive second portion 50B therein. In addition, first portion 50A may include a distal lip or rim 53 cooperative with a distal end 55 of second portion 50B. A rotatable seal portion 50C may be disposed between first portion 50A and second portion 50B and may enable rotational movement of first portion 50A relative to second portion 50B. Accordingly, first portion 50A may be coupled to insertion device 80 and may rotate with respect to second portion 50B coupled to slot body 16.

In use, pin 40 may be positioned within slot track 28 of slot body 16. In order to extend end effector 14 distally of working channel 82, thereby enabling end effector 14 to radially expand, pin body 18 may be urged distally such that pin 40 travels along channel 29 through distance D towards tab 32. Once positioned within channel 29 adjacent tab 32, pin body 18 may be rotated such that pin 40 enters tab 32. In such a manner, pin 40 may be retained within tab 32, thereby maintaining end effector 14 in the expanded configuration. However, upon further rotation of pin 40 toward and into tab 32, pin 40 may contact and then urge slot body 16 to rotate with pin 40 and pin body 18. Due to the connection of pin body 18 to tool body 70 via grommet 74 (see, for example, FIG. 2), continued rotation of pin body 18 results in rotation of tool member 70 and end effector 14. Additionally, as slot body 16 is coupled to second portion 50B of connector, which is in turn, rotatable with respect to first portion 50A coupled to insertion device 80, continued rotation of pin body 18, which urges slot body 16 to rotate, results in rotation of end effector 14 and slot body 16 with respect to insertion device 80.

The disclosed medical device 10 may enable quick and accurate extension and retraction of tool body 70 relative to an insertion device. Tabs 32, 34, 36, and 38 may define incremental, accurately repeatable degrees of extension and retraction tool body 70 to ensure proper placement for manipulation by a medical professional. The distance between, number, and arrangement of tabs 32, 34, 36, and 38 may enable a variety of incremental distances allowing selection of a desired extension length of tool body 70. Additionally, while not shown, any one or more of pin body 18, slot body 16, connector 50, or other such component of medical device 10 may include a funnel or taper therein to facilitate insertion of tool body 70 therein.

While principles of the present disclosure are described herein with reference to illustrative examples for particular applications, it should be understood that the disclosure is not limited thereto. Those having ordinary skill in the art and access to the teachings provided herein will recognize additional modifications, applications, embodiments, and substitution of equivalents all fall within the scope of the features described herein. Accordingly, the claimed features are not to be considered as limited by the foregoing description.

We claim:

1. A medical device, comprising:
    a tool body; and
    a handle, the handle comprising:
        a first body having a first coupling feature extending axially along the first body, the first coupling feature including a channel communicating with a first plurality of tabs extending from the channel in a first direction and a second plurality of tabs extending from the channel in a second direction different than the first direction, wherein the first coupling feature includes a release slot extending parallel with a longitudinal axis of the first body from an end of a first tab opposite that of the channel, wherein the first tab is a distal-most tab of the first plurality of tabs and wherein the release slot extends distally from the end of the first tab; and
        a second body including a second coupling feature positioned within the first coupling feature;
    wherein, in a first orientation, the first body and second body are rotatable and axially translatable relative to each other as a function of the first and second coupling features.

2. The medical device of claim 1, wherein the first coupling feature forms a through hole extending through a circumferential surface of the first body.

3. The medical device of claim 2, wherein each of the first plurality of tabs and the second plurality of tabs extend radially outwardly from the channel.

4. The medical device of claim 2, wherein the first plurality of tabs are equispaced from one another and wherein the second plurality of tabs are equispaced from one another.

5. The medical device of claim 1, wherein the release slot has a proximal end extending from the end of the first tab and a distal end, wherein the release slot is configured such that advancement the second coupling feature from the proximal end of the release slot toward the distal end of the release slot enables over-expansion of an end-effector of the tool body.

6. The medical device of claim 1, wherein the second coupling feature includes a pin.

7. The medical device of claim 6, wherein the pin is positioned on a cantilevered support of the second body.

8. The medical device of claim 1, wherein the handle further includes a biasing member.

9. The medical device of claim 8, wherein the biasing member is positioned within the first body and the second body.

10. The medical device of claim 1, further including a cap coupled to a proximal end of the second body, and a grommet positioned about the tool body and arranged between the cap and the proximal end of the second body.

11. A medical device, comprising:
a tool body terminating in an end effector; and
a handle, the handle comprising:
a first body having a track extending axially along the first body and a release slot in communication with, and extending parallel to, the track; and
a second body coupled to the first body and including a pin positioned within the track;
wherein, in a first configuration, the end effector extends out of a working channel of the medical device and the pin is located at a first axial position along the track;
wherein, in a second configuration, the end effector is positioned within the working channel of the medical device and the pin is located at a second axial position along the track, wherein the first axial position is distal of the second axial position; and
wherein, in a third configuration, the end effector is arranged in an expanded-most configuration and the pin is located along the release slot, wherein the release slot extends distally from a distal-most tab in communication with the track.

12. The medical device of claim 11, wherein the track includes a through hole extending through a circumferential surface of the first body and includes a channel and a plurality of tabs extending from the channel, wherein the distal-most tab is one of the plurality of tabs and includes a first tab end terminating at the channel and a second tab end terminating at the release slot.

13. The medical device of claim 12, wherein the plurality of tabs are equispaced from one another.

14. The medical device of claim 12, wherein the plurality of tabs includes a first plurality of tabs and a second plurality of tabs, wherein each of the first plurality of tabs extends in a first direction and each of the second plurality of tabs extends in a second direction from the channel.

15. The medical device of claim 11, further including a cap coupled to a proximal end of the second body, and a grommet positioned about the tool body and arranged between the cap and the proximal end of the second body, wherein in a first grommet configuration, the tool body may be moved axially relative to the grommet, and wherein in a second grommet configuration, the tool body may be locked axially relative to the grommet.

16. The medical device of claim 12, wherein the pin is positioned on a cantilevered support of the second body.

17. The medical device of claim 12, wherein the handle further includes a biasing member positioned within the first body and the second body.

18. A method, including:
delivering a tool body of a medical device through a working channel of an insertion device, the medical device including a first body and a second body;
moving a pin coupled to the second body distally along a channel of a track positioned on the first body and extending the tool body of the medical device out of the working channel of the insertion device;
rotating the second body relative to the first body to position the pin within a distal tab of the track extending radially outwardly of the channel of the track; and
moving the pin distally along a release slot, wherein the release slot extends distally and parallel with a longitudinal axis of the first body from an end of the distal tab opposite that of the channel.

19. The method of claim 18, further including proximally retracting the pin along the release slot to align the pin with the distal tab, rotating the second body relative to the first body to position the pin within the channel of the track, and proximally retracting the pin along the channel of the track to retract the tool body relative to the working channel of the insertion device.

20. The method of claim 19, wherein retracting the tool body relative to the working channel of the insertion device includes aligning a distal-most end of the tool body with a distal-most end of the working channel; and
further including axially securing the tool body relative to the second body via a grommet.

* * * * *